(12) United States Patent
Coppens

(10) Patent No.: US 10,682,445 B2
(45) Date of Patent: *Jun. 16, 2020

(54) IMMOBILIZER PREFORM, IMMOBILIZER DEVICE, AND METHOD OF FORMING THE SAME

(71) Applicant: QFIX SYSTEMS, LLC, Avondale, PA (US)

(72) Inventor: Daniel Coppens, Avondale, PA (US)

(73) Assignee: Qfix Systems, LLC, Avondale, PA (US)

( * ) Notice: Subject to any disclaimer, the term of this patent is extended or adjusted under 35 U.S.C. 154(b) by 349 days.

This patent is subject to a terminal disclaimer.

(21) Appl. No.: 15/693,745

(22) Filed: Sep. 1, 2017

(65) Prior Publication Data

US 2017/0360995 A1 Dec. 21, 2017

Related U.S. Application Data

(63) Continuation of application No. 14/134,685, filed on Dec. 19, 2013, now Pat. No. 9,775,934.
(Continued)

(51) Int. Cl.
*A61L 31/06* (2006.01)
*A61L 31/14* (2006.01)
(Continued)

(52) U.S. Cl.
CPC .............. *A61L 31/06* (2013.01); *A61F 5/058* (2013.01); *A61F 5/3707* (2013.01);
(Continued)

(58) Field of Classification Search
CPC ........ A01N 25/10; A01N 37/46; A01N 63/02; A61L 15/585; A61L 15/07; A61L 15/12;
(Continued)

(56) References Cited

U.S. PATENT DOCUMENTS 5,074,292 A 12/1991 Cox
5,775,337 A 7/1998 Hauger et al.
(Continued)

FOREIGN PATENT DOCUMENTS

DE 102005026298 A1 12/2006
EP 1029521 A2 8/2000
(Continued)

OTHER PUBLICATIONS

European Communication Pursuant to Article 94(3) EPC for European Application No. 13824709.3, dated Sep. 28, 2017, 5 pages.
(Continued)

*Primary Examiner* — Tarla R Patel
(74) *Attorney, Agent, or Firm* — RatnerPrestia

(57) ABSTRACT

Aspects of the invention include preforms used to be formed into an immobilizer for use with a patient. The preform includes a preform member that is formed from a thermoplastic material and a filler material. The preform member is relatively rigid at a first temperature and formable at an elevated second temperature. The preform member is opaque at the first and second temperatures. The preform also includes at least one indicator associated with the preform member. The at least one indicator is formed from a thermoplastic material and is opaque at the first temperature and translucent at the second temperature. The at least one indicator can provide a visual indication of readiness to form the preform into the immobilizer upon heating the preform member to the second temperature at which the indicator is translucent.

19 Claims, 10 Drawing Sheets

Related U.S. Application Data

(60) Provisional application No. 61/746,931, filed on Dec. 28, 2012.

(51) Int. Cl.
*B29C 51/46* (2006.01)
*A61F 13/04* (2006.01)
*A61F 13/02* (2006.01)
*A61F 5/058* (2006.01)
*A61F 5/37* (2006.01)

(52) U.S. Cl.
CPC .......... *A61F 13/0293* (2013.01); *A61F 13/04* (2013.01); *A61L 31/14* (2013.01); *B29C 51/46* (2013.01)

(58) Field of Classification Search
CPC .......... A61L 15/14; A61L 15/42; A61L 15/60; A61L 2202/23; A61L 2202/24; A61L 2/07; A61L 2/081; A61L 2/087; A61F 13/04; A61F 2/0811; A61F 2/08; A61F 5/01; A61F 5/058; A61F 5/05825; A61F 13/00063; A61F 13/511; A61F 2220/0016; A61F 13/00068; A61F 13/51305; A61F 13/8405; A61F 2002/30242
USPC ........................................................ 602/5–8
See application file for complete search history.

(56) References Cited

U.S. PATENT DOCUMENTS

| | | | |
|---|---|---|---|
| 6,358,220 | B1 | 3/2002 | Langen et al. |
| 6,854,140 | B2 | 2/2005 | Bartels et al. |
| 9,775,934 | B2 * | 10/2017 | Coppens ................. A61F 13/04 |
| 2002/0095722 | A1 | 7/2002 | Korver et al. |
| 2004/0143905 | A1 | 7/2004 | Pastyr et al. |
| 2008/0086068 | A1 | 4/2008 | Langen et al. |
| 2011/0172575 | A1 | 7/2011 | Langen |

FOREIGN PATENT DOCUMENTS

| | | |
|---|---|---|
| WO | 02076298 A2 | 10/2002 |
| WO | 2007120855 A2 | 10/2007 |
| WO | 2009131818 A2 | 10/2009 |

OTHER PUBLICATIONS

European Communication for European Application No. 13824709.3, dated May 20, 2019, 6 pages.
International Search Report and Written Opinion for International Application PCT/US2013/077513, dated Mar. 20, 2014, 9 Pages.
International Preliminary Report on Patentability for International Application No. PCT/US2013/077513, dated Jun. 30, 2015, 7 Pages.
Extended European Search Report for European Application No. 13844336.1, dated Mar. 17, 2017, 8 pages.
Entire patent prosecution history of U.S. Appl. No. 14/134,685, filed Dec. 19, 2013, entitled, "Immobilizer Preform, Immobilizer Device, and Method of Forming the Same."

* cited by examiner

IMMOBILIZER PREFORM, IMMOBILIZER DEVICE, AND METHOD OF FORMING THE SAME

CROSS REFERENCE TO RELATED APPLICATION

This application is a continuation of U.S. patent application Ser. No. 14/134,685, filed Dec. 19, 2013, which claims priority of Provisional Application No. 61/746,931 ("Low Temperature Thermoplastic With Unfilled Sections Such That Temperature And Readiness To Mold Can Be Monitored") filed on Dec. 28, 2012, the entire disclosures of which are incorporated herein by reference in their entirety for all purposes.

BACKGROUND OF THE INVENTION

There is a growing need for improved devices that can immobilize patients or patient anatomies. For example, thermoplastic sheets are known and used as patient immobilizers in radiation therapy to reduce or prevent movement of patient anatomies during therapy. Such sheets are heated to become formable, formed over a part of a patient's anatomy, and then cooled to harden, thereby immobilizing the patient or patient's anatomy for the treatment therapy.

Despite developments that have been made in connection with such devices, there remains a need for improved patient immobilizers as well as improved methods and processes for immobilizing patients in terms of at least one of cost control, enhanced performance, and ease of use.

SUMMARY OF THE INVENTION

Aspects of the invention include preforms used to be formed into an immobilizer for use with a patient. The preform includes a preform member that is formed from a thermoplastic material and a filler material. The preform member is relatively rigid at a first temperature and formable at an elevated second temperature. The preform member is opaque at the first and second temperatures. The preform also includes at least one indicator associated with the preform member. The indicator has an appearance at the first temperature and a different appearance at the second temperature, wherein the indicator provides a visual indication of readiness to form the preform into the immobilizer upon heating the preform member to the second temperature at which the indicator has the different appearance. For example, the at least one indicator is optionally formed from a thermoplastic material and is opaque at the first temperature and translucent at the second temperature. When the at least one indicator is formed from a thermoplastic material that is opaque at the first temperature and translucent at the second temperature, the at least one indicator provides a visual indication of readiness to form the preform into the immobilizer upon heating the preform member to the second temperature at which the indicator is translucent. Alternatively, the at least one indicator is optionally formed from a material including a thermochromic dye or other color indicator that can provide a different appearance at the second temperature.

Aspects of the invention also include methods of preparing a preform to be formed into an immobilizer for a patient. A preform member of the preform is heated from a first temperature at which the preform member is relatively rigid to a second temperature at which the preform member can be molded. The preform member includes a thermoplastic material and a filler material and is opaque at the first and second temperatures. An indicator associated with the preform member is monitored during the heating of the preform member. The indicator has an appearance at the first temperature and a different appearance at the second temperature, wherein the indicator provides a visual indication of readiness to form the preform into the immobilizer upon heating the preform member to the second temperature at which the indicator has the different appearance. The indicator is optionally formed from a thermoplastic material that is opaque at the first temperature and translucent at the second temperature. When the indicator is formed from a thermoplastic material that is opaque at the first temperature and translucent at the second temperature, the heating of the preform member is terminated after the indicator becomes translucent, providing a visual indication of the readiness to form the preform into the immobilizer. Alternatively, the at least one indicator is optionally formed from a material including a thermochromic dye or other color indicator that can provide a different appearance at the second temperature. The heating of the preform member is terminated after the indicator has the different appearance, providing a visual indication of the readiness to form the preform into the immobilizer.

Aspects of the invention also include immobilization devices with multiple sections formed from polycaprolactone low temperature thermoplastic. The immobilization device includes at least one preform section that does not become translucent when heated to its melting point, the preform section being formed from the polycaprolactone low temperature thermoplastic and a filler material. The immobilization device also includes at least one indicator section. The indicator section has an appearance at a first temperature and a different appearance at a second temperature, wherein the indicator section provides a visual indication of readiness to form the preform section into the immobilization device upon heating the preform section to the second temperature at which the indicator section has the different appearance. For example, the indicator section optionally becomes translucent when heated to its melting point. Alternatively, the at least one indicator section is optionally formed from a material including a thermochromic dye or other color indicator that can provide a different appearance at the second temperature.

BRIEF DESCRIPTION OF THE DRAWINGS

The invention is best understood from the following detailed description when read in connection with the accompanying drawings, with like elements having the same reference numerals. When a plurality of similar elements is present, a single reference numeral may be assigned to the plurality of similar elements with a small letter designation referring to specific elements. Included in the drawings are the following figures.

DETAILED DESCRIPTION OF THE INVENTION

Figure 1:
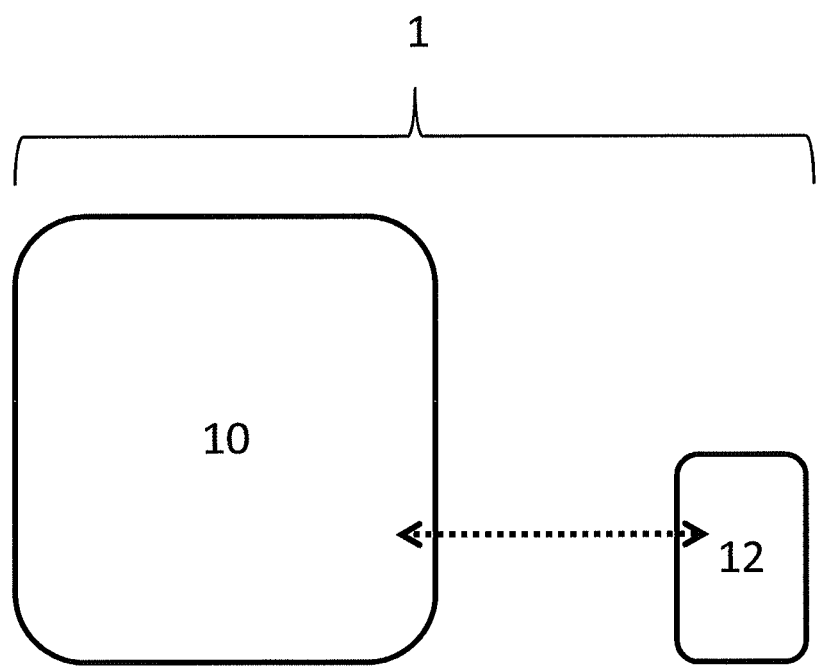
FIG. 1 is a schematic diagram depicting an embodiment of a preform according to aspects of the invention.

Although the invention is illustrated and described herein with reference to specific embodiments, the invention is not intended to be limited to the details shown. Rather, various modifications may be made in the details within the scope and range of equivalents of the claims and without departing from the invention.

Referring to the figures generally, the invention provides preforms, such as preforms 1, 2, 3, and 4, used to be formed into an immobilizer for use with a patient. The preform includes a preform member, such as preform members 10, 30, 50, and 70, that is formed from a thermoplastic material and a filler material. The preform member is relatively rigid at a first temperature and formable at an elevated second temperature. The preform member is opaque at the first and second temperatures. The preform also includes at least one indicator, such as indicators 12, 26, 34, 36, 38, 52, 62, and 72, associated with the preform member. The indicator has an appearance at the first temperature and a different appearance at the second temperature, wherein the indicator provides a visual indication of readiness to form the preform into the immobilizer upon heating the preform member to the second temperature at which the indicator has the different appearance. For example, the at least one indicator is optionally formed from a thermoplastic material that is opaque at the first temperature and translucent at the second temperature. When the at least one indicator is formed from a thermoplastic material that is opaque at the first temperature and translucent at the second temperature, the at least one indicator provides a visual indication of readiness to form the preform into the immobilizer upon heating the preform member to the second temperature at which the indicator is translucent. Alternatively, the at least one indicator is optionally formed from a material including a thermochromic dye or other color indicator that can provide a different appearance at the second temperature.

The preform member can be opaque or substantially opaque at the first and second temperatures. For example, the preform member can have substantially the same degree of opacity or imperviousness to light at the first and second temperatures. In contrast, the indicator can be opaque or substantially opaque at the first temperature and translucent or substantially translucent at the second temperature. For example, the indicator can have a lesser degree of opacity or imperviousness to light at the second temperature as compared to at the first temperature, and the indicator can have a greater degree of translucence at the second temperature as compared to at the first temperature.

The preform may include a frame member, such as frame member 24, 32, and 60, associated with the preform member, with the indicator being coupled to at least one of the frame member or the preform member. The indicator can be positioned on at least one of a surface portion of the frame member, if the preform includes a frame member, or a surface portion of the preform member, such that the at least one surface portion is not visible through the indicator when the indicator is at the first temperature and is visible through the indicator when the indicator is at the second temperature.

The preform may also include an indicium, such as indicium 64 and 82, positioned on at least one of the surface portion of the frame member, the surface portion of the preform member, a surface portion of the indicator, or disposed within the indicator, the indicium not being visible through the indicator when the indicator is at the first temperature and being visible through the indicator when the indicator is at the second temperature. The surface portion of the frame or preform member can at least partially define a recess formed in the frame member or preform member.

Generally, one way of improving the materials used to form a preform is to add fillers that enhance material properties. However, these additives often prevent the material from becoming substantially translucent at forming temperatures. There is, therefore, a need for an indicator to allow the user to know when the material is ready to form. Having an indicator allows the user to ensure that a high quality immobilization device can be produced in a minimum amount of time.

Referring specifically to FIG. 1, an embodiment of a preform is shown schematically as preform 1. The preform 1 includes a preform member 10 and an indicator 12 that is associated with the preform member 10. The preform 1 is configured to be formed into an immobilizer for use with a patient and is exposed to a first temperature and an elevated second temperature. At the first temperature, the preform member 10 is relatively rigid and the preform member 10 and indicator 12 are opaque. At the second temperature, the preform member 10 is less rigid and can be molded, remaining opaque, while the indicator 12 is relatively translucent with respect to the preform member 10. The translucent indicator 12 provides a visual indication as to the readiness of the preform 1 to be formed into the immobilizer. When the preform 1 is cooled from the second temperature, the indicator 12 turns from translucent to opaque, thereby providing visual indication of the completion of forming the immobilizer. The indicator may turn opaque prior to the material being cooled to room temperature. Therefore, the indicator may indicate that the immobilizer is approaching readiness to be removed from the patient and that it will be ready soon when it reaches room temperature. Accordingly, the use of the indicator upon cooling is optional.

The indicator 12 is associated with the preform member 10 such that the indicator 12 is exposed to the first and second temperatures concurrently or substantially simultaneously as the preform member 10. The indicator 12 may be associated by being detached from and located proximal to the preform member 10, coupled to the preform member 10, attached to the preform member 10, positioned on a surface of the preform member 10, disposed within the preform member 10, etc. Other associations between the indicator 12 and the preform member 10 for effectuating the invention will be understood by one of skill in the art from the description herein.

Figure 2:
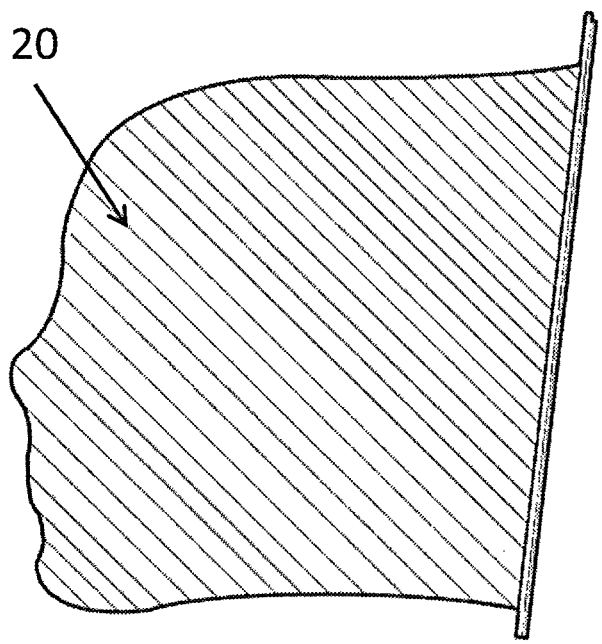
FIGS. 2 and 3 depict various applications of a preform being formed into an immobilizer for use with a patient's anatomy according to aspects of the invention.
Figure 3:
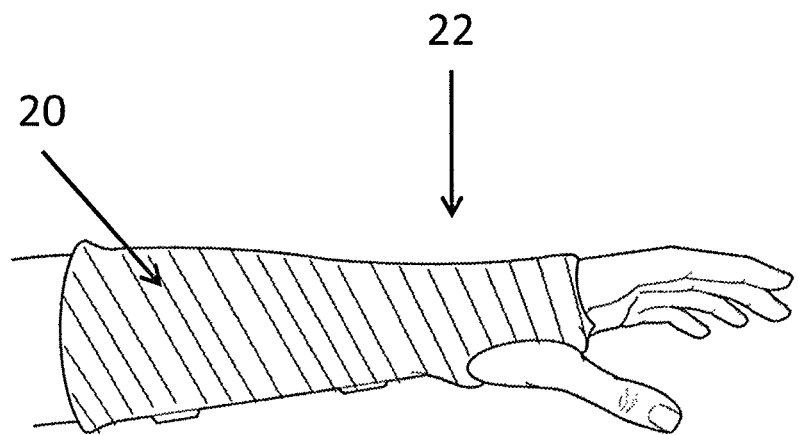

FIGS. 2 and 3 are depictions of various embodiments in which a preform member of a preform, illustrated as preform member 20, can be molded for use as patient immobilization devices. The preform member 20 may be used to form around various parts of a patient's anatomy. As depicted in FIG. 2, the preform member 20 is molded over the head portion of a patient. In FIG. 3, the preform member 20 is molded around an arm of a patient, thereby forming a cast or splint 22. The preform member 20 may be formed around the shoulders of a patient, the chest of a patient, the waist of a patient, the legs of a patient, etc. Other parts of a patient's anatomy around which the preform member 20 may be formed will be understood by one of skill in the art from the description herein. Additionally, the immobilization device formed from a preform according to this invention may be used for applications other than patient immobilization as well. For example, an immobilization device according to this invention can be used for manufacturing processes, construction structures, artistic creations, and a wide variety of other uses.

Figure 4:
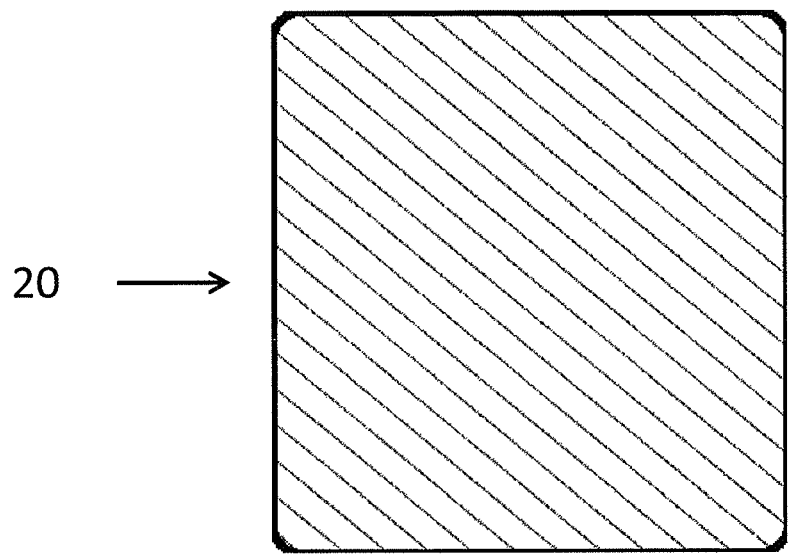
FIG. 4 is a representation of an embodiment of a preform member in accordance with aspects of the invention.

Referring next to FIG. 4, a preform member 20 formed from thermoplastic material and a filler material is shown. In one embodiment, the thermoplastic material includes a Polycaprolactone-based (PCL) low temperature thermoplastic.

Polycaprolactone (PCL) based low temperature thermoplastics are suitable for use in a wide range of medical applications such as splinting, casting and molding for applications in Radiation Therapy and Orthopedics. The material is typically heated in a water bath or in an oven or by other application of heating energy to its melting point and is then formed around the patient's anatomy to make a custom formed device. The material is optionally partially cross-linked prior to heating. Such partial cross-linking improves the usability of the preform member.

One feature of such thermoplastic materials is that in their unfilled form, they change from a milky white color to substantially translucent when heated to their melting point (approximately 140° F./60° C.). Such unfilled material can be used as an indicator that the material is ready to be formed to the patient's anatomy. This can work much like the "pop-up timer" on a supermarket turkey, letting the user know that the "cooking" is complete.

It is contemplated that the preform member 20 may be formed from multiple thermoplastic materials and/or a combination of thermoplastic materials and non-thermoplastic materials. Also, materials other than thermoplastic materials can be used to form preform member 20, but such other materials are preferably selected from materials that are relatively rigid at a first temperature and relatively less rigid, or formable, at an elevated second temperature.

The preform member 20 additionally includes at least one filler material together with the thermoplastic base material. In order to improve the physical performance of the PCL material (i.e. stiffness and strength) as well as for aesthetic reasons, it is often desirable to add fillers to these materials. Fillers can include, but are not limited to, materials such as talc, aramid (KEVLAR®), dyes, nanoparticles, carbon fiber, fiberglass, polyurethane, fumed silica, high stiffness additives, etc.

Additionally, a thermochromic dye is optionally added to the base material or to the frame. For such a dye, a temperature can be selected that is near, above or below the softening temperature of the base material. Also, the dimensions of the base material and temperature characteristics of such a dye can be selected such that a temperature change of the surface of the base material would match the actual core temperature of the base material.

While these fillers impart desirable characteristics to the preform, they keep the materials from turning clear or translucent when heated to a molding temperature. Hence, preform members formed from filled material do not provide a visible indication of when the material is ready to be molded.

Figure 5:
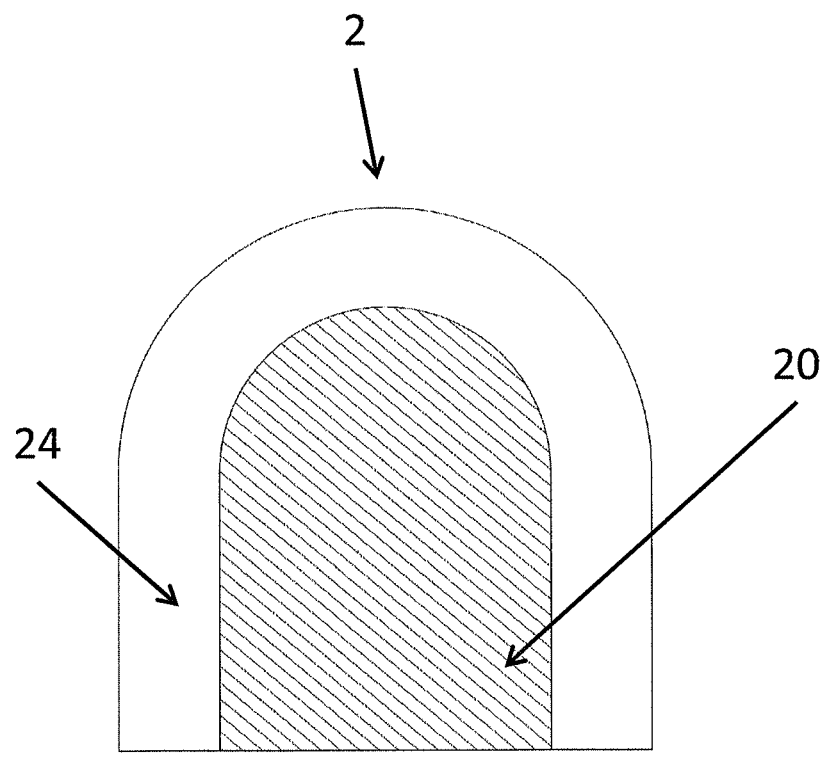
FIG. 5 is a top view of an embodiment of a preform in accordance with aspects of the invention.

Referring next to FIG. 5, an embodiment of a preform 2 is shown. The preform 2 includes the preform member 20 that is positioned within a frame member 24. In many applications the PCL thermoplastic preform member 20 is mounted to a rigid thermoplastic (TP) frame member 24 (typically formed from ABS or another suitable material). The frame member 24 is preferably formed from a material that does not soften when heated to 140 F (i.e., approximately the second temperature at which the preform member 20 can be molded), the melting point of PCL. This allows the assembly (i.e., preform 2) to be mounted to various other devices.

Figure 6A:
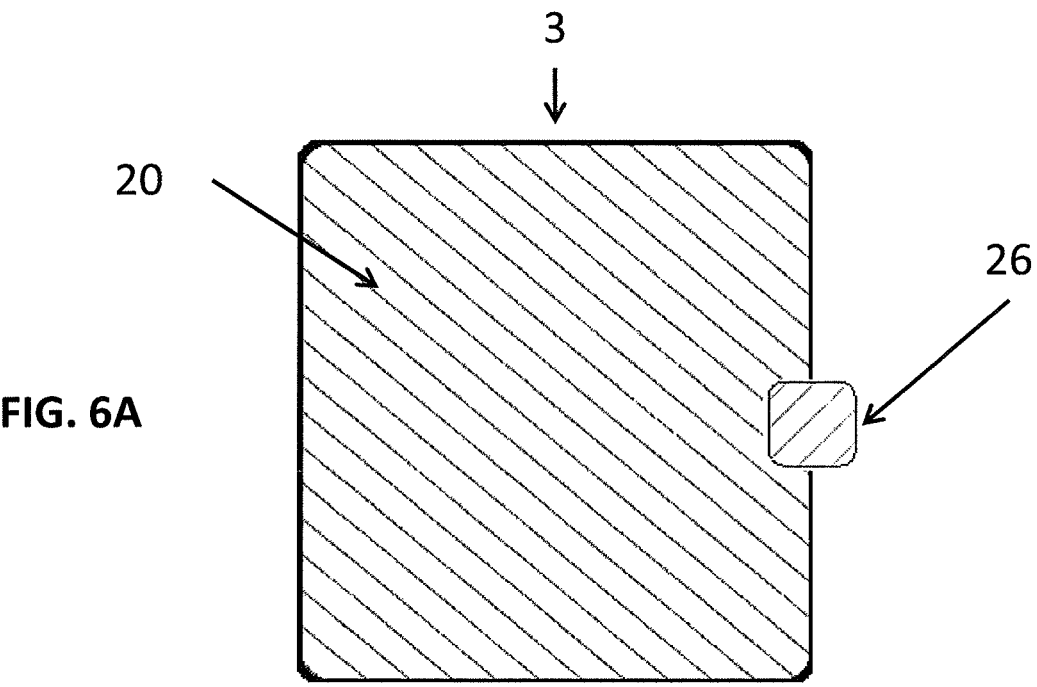
FIGS. 6A and 6B illustrate an embodiment of a preform member and indicator according to aspects of the invention.
Figure 6B:
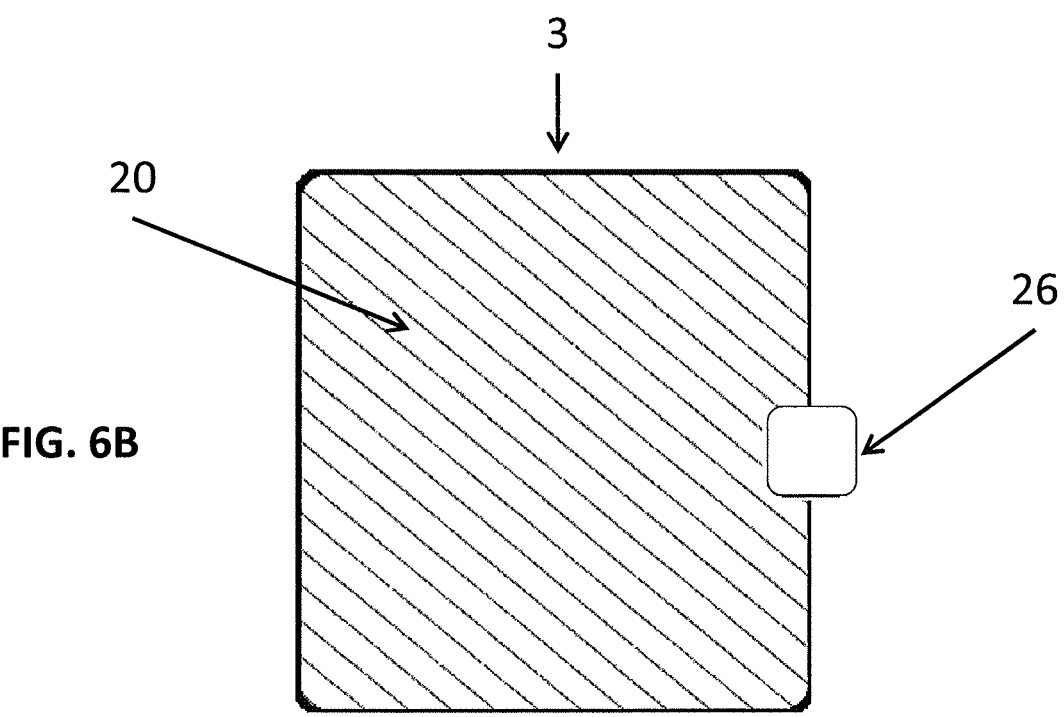

At FIGS. 6A and 6B, an embodiment of a preform 3 with the preform member 20 and an indicator 26 associated with the preform member 20 is shown. The indicator 26 may be formed from a thermoplastic material, such as PCL-based material. In one embodiment, the indicator 26 is formed with no filler material or at least less filler material than that of the preform member 20.

As depicted in FIG. 6B, the indicator 26 may be formed of a material such that the indicator 26 becomes translucent with respect to the preform member 20 when the indicator 26 is heated to the second temperature. In order to take advantage of the characteristics of the filled materials in the preform member 20 as discussed above with respect to FIG. 4, while providing visual feedback to the user regarding the readiness of the preform for forming an immobilization device, the preform preferably includes a section of unfilled material (i.e., the indicator 26 in the embodiment illustrated in FIGS. 6A and 6B) within a device (i.e., preform 3 in the embodiment illustrated in FIGS. 6A and 6B) constructed primarily of filled materials (i.e., the preform member 20 in the embodiment illustrated in FIGS. 6A and 6B).

As used herein, the term "unfilled" and "unfilled material" refers to a material that is less filled (as compared to the remainder of the preform member 20 for example) such that the unfilled material becomes more translucent as compared to the remainder of the preform member 20 when heated to the second temperature. This unfilled section allows the user to easily determine when the device (e.g., preform 3) has reached the melting temperature (e.g., the second temperature).

The section of unfilled material can be strategically placed such that it does not negatively affect the beneficial properties of the filled material. For example, the unfilled material that serves as an indicator can be placed in locations where strength or stiffness is less important. In fact, a combination of filled and unfilled sections may be employed to impart beneficial properties such as selective reinforcement combined with the ability to determine molding readiness.

It is desirable that the section of unfilled material not indicate that the material is ready until the filled material reaches or approaches its melting temperature. Several strategies can be followed to achieve this result. For example, the section of unfilled material can be made of a size, volume or thickness on the order of magnitude of that of the surrounding material so that it has a similar mass and heat absorption. In other words, the properties of the indicator in connection with the timing for reaching a target temperature such as its melting temperature is preferably matched with the corresponding properties of the filled material. By doing so, the indicator will accurately reflect when the filled portion is ready for molding. If the same base material is used for the filled and unfilled portions, the primary variables will include the respective sizes of the filled and unfilled portions (e.g., their respective thicknesses). If the base materials for the filled and unfilled portions are different, then the variables will also include the respective properties of the base materials and how they may impact timing for readiness for molding or forming.

The unfilled elements of the embodiment shown in FIGS. 6A and 6B can be of virtually any shape as long as the fact that they become clear (or become at least partially translucent as compared to the preform member 20 and/or devices 1, 2, 3) is easy to visualize by the user. Viable shapes include but are not limited to squares, rectangles, circles, ovals, hexagons, strips, aesthetically desirable shapes, source-identifiers, and so forth. The unfilled elements may be perforated or not perforated. In an embodiment, the indicator 26 (i.e., unfilled element) is formed into the shape of an alphanumeric character. In one embodiment, the indicator 26 is of a color that is different than a color of the preform member 20 and/or other components of the preform (1,2,3) at the first temperature, the second temperature, or both, so as to provide sufficient visual indication as to the readiness of the preform to be molded and/or the location of the indicator.

FIGS. 6A and 6B illustrate the contrast between a filled portion of a preform (such as preform member 20 of preform 3) and an unfilled portion of a preform (such as indicator 26 of preform 3). In a first condition when the preform 3 has not been heated (such as when it is at an ambient or room temperature), there is a smaller degree of contrast between the appearances of preform member 20 and indicator 26. For example, although there may or may not be a difference in the colors of the preform member 20 and indicator 26, preform member 20 and indicator 26 may have the similar or same degree of transparency or opaqueness.

In a second condition when the preform 3 has been heated (such as when it is exposed to heat by heated fluid or another heat source), there is a larger degree of contrast between the appearances of preform member 20 and indicator 26. For example, preform member 20 and indicator 26 will have a degree of transparency or opaqueness. In one embodiment, preform member 20 may be partially or completely opaque and indicator 26 may be partially or completely translucent, thus increasing the contrast in the appearance of the preform member 20 and indicator 26 at a second condition of elevated temperature.

Referring next to FIGS. 7-9D, various shapes, sizes, and positions of indicators positioned on a preform 4 are depicted. Each embodiment of the preform 4 includes a preform member 30 substantially as described with respect to preform member 20 and a frame member 32 substantially as described with respect to frame member 24. The preform 4 may include one indicator or a plurality of indicators.

Figure 7:
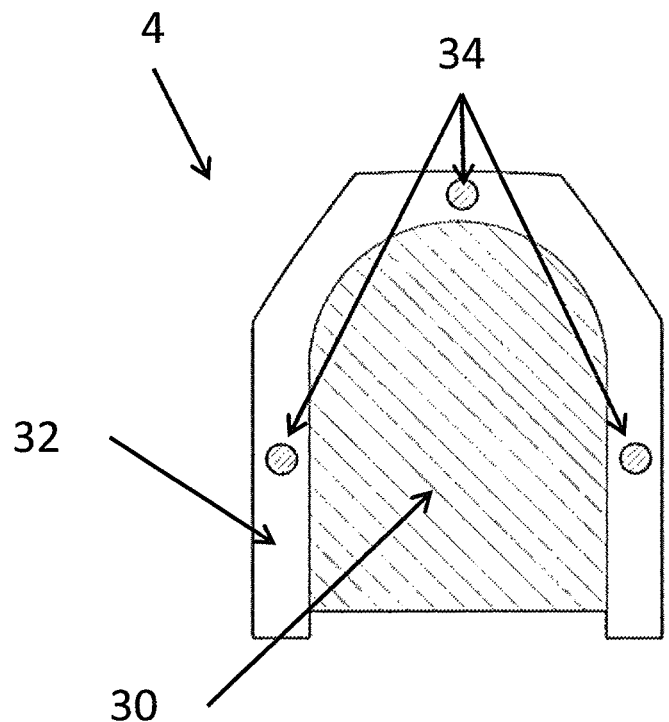
FIGS. 7-9D are top views of embodiments of preforms with indicators in various positions according to aspects of the invention.

As depicted in FIG. 7, indicators 34 are coupled to the frame member 32. The indicators 34 are positioned on the surface of the frame member 32 and may be positioned within recesses formed in the frame member 32. In one embodiment, the frame member 32 defines one or more apertures (not shown) and the indicators 34 are positioned to traverse the aperture(s).

Figure 8:
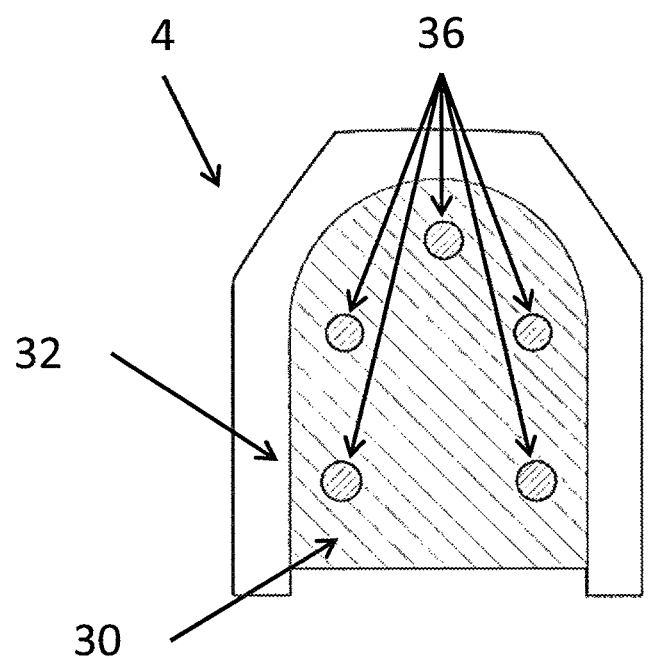

In FIG. 8, indicators 36 are coupled to the preform member 30. The indicators 36 may be positioned on the surface of the preform member 30. In one embodiment, the indicators 36 are positioned within recesses formed on the preform member 30 as will be described with respect to FIGS. 10A-10C.

Figure 9A:
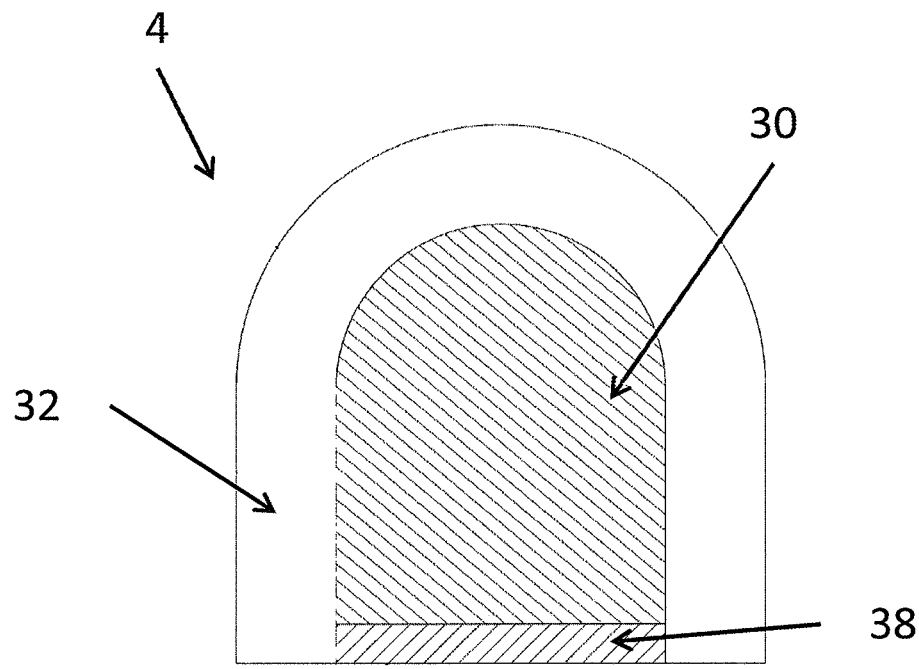

In one preferred embodiment, at least one unfilled section of material is butt-welded or otherwise directly connected to a filled section of material. The unfilled material can be placed in any position and can be strategically positioned to maximize the benefits of the filled material. For example, FIG. 9A shows one preferred embodiment in which the unfilled material (i.e., indicator 38 in the illustrated embodiment) is placed at the bottom of a Radiation Therapy Patient Positioning mask. The indicator 38 may extend fully or partially across the width of the preform member 30. In an alternative embodiment (not shown), the indicator 38 may extend vertically across the preform member 30. Other suitable orientations and extensions of the indicator 38 with respect to the embodiment depicted in FIG. 9A will be understood by one of skill in the art from the description herein.

Figure 9B:
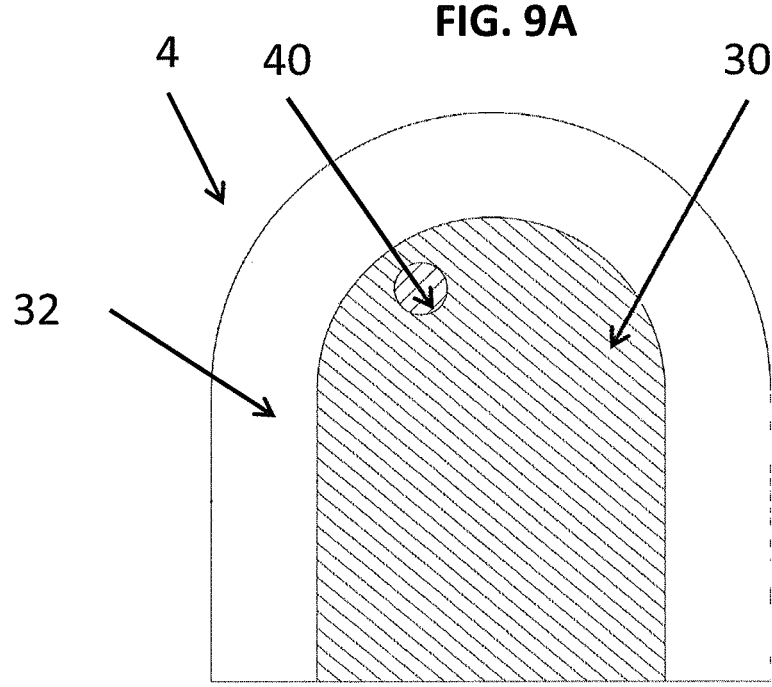

Alternatively, the clear or unfilled material 40 can be embedded in the surrounding material 30 such that it must heat up along with the surrounding material (see, for example, the embodiment illustrated in FIG. 9B, in which an indicator of unfilled material 40 is optionally positioned such that it is partially or completely surrounded by the filled material 30).

The unfilled material 40 may also be solid (not perforated) while the filled material 30 is perforated so that the unfilled material 40 area still has higher heat capacity. In this way, the indicator can be configured such that it will arrive at an elevated target temperature after the filled material to ensure readiness of the unfilled material for forming.

Figure 9C:
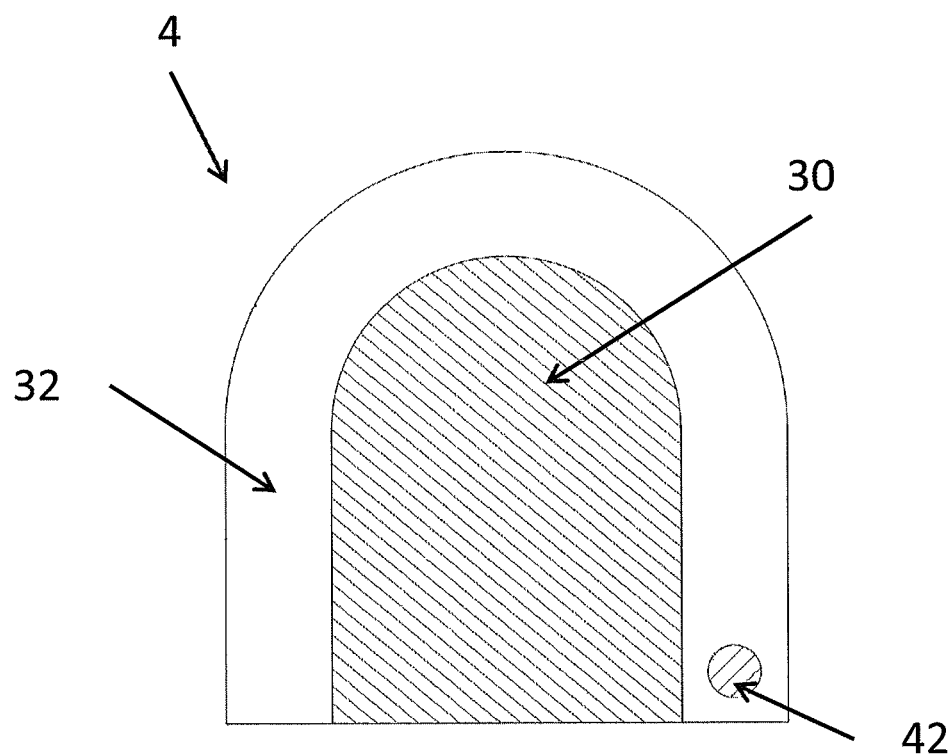

An additional strategy is to embed the unfilled material 42 in the frame member 32 of the device 4 (see, for example, the embodiment illustrated in FIG. 9C, in which an indicator of unfilled material 42 is optionally positioned such that it is partially or completely surrounded by the frame member 32).

These strategies ensure that the unfilled material 34, 36, 38, 40, 42, 44 will not heat up more quickly than the filled material 30 and hence turn clear too early.

As described with respect to FIG. 5, the frame member 32 does not soften when heated to the second temperature. In these instances, the thermoplastic frame member 32 can have a section of unfilled PCL material 42 embedded in it as shown in FIG. 9C. This is a preferred embodiment as it is surrounded by a solid polymer, slowing down the heat transfer to the section. In this way, it is the last part of the system to reach molding temperature and ensures that the unfilled preform member has reached the necessary temperature for molding and forming. In some cases, there may be portions of the device (e.g., the frame) that have not reached the optimum temperature (e.g., thicker sections, ribs).

Figure 9D:
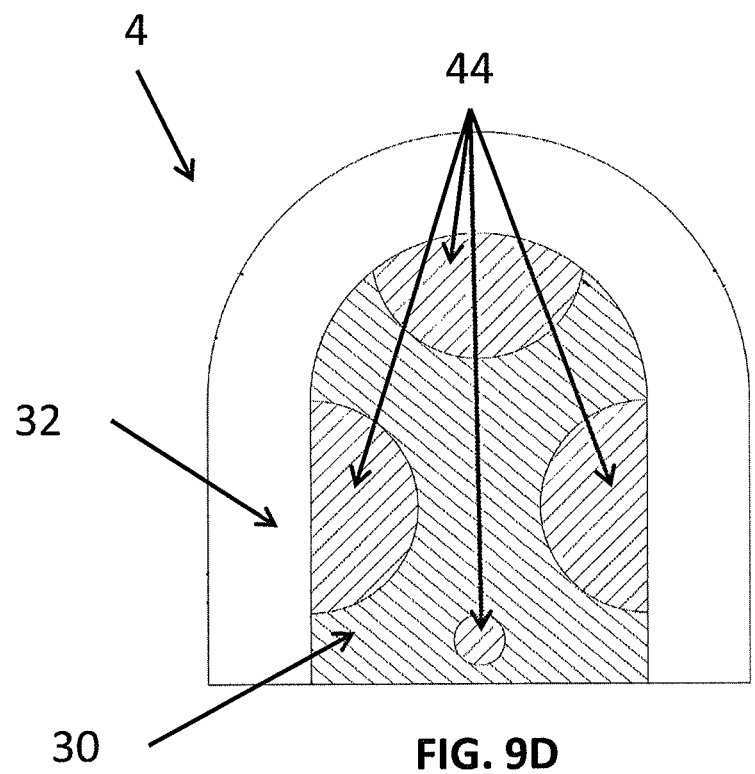

In another exemplary embodiment, the filled 30 and unfilled 44 sections of PCL are arranged substantially similar to the arrangement shown in FIG. 9D. An arrangement of this nature maximizes the effects of the rigid filled PCL 30 by placing it such that the filled PCL 30 will create a rigid mask. The areas of unfilled PCL 44 provide feedback to the user when the mask has reached its melting temperature.

Figure 10A:
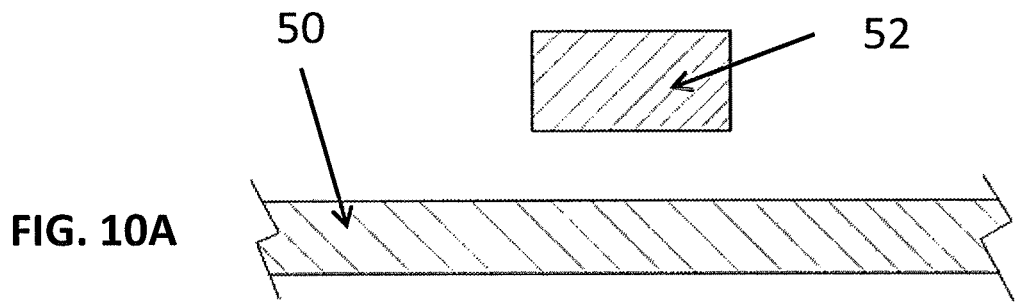
FIGS. 10A-10C are cross-sectional side views of embodiments of preform members and indicators in accordance with aspects of the invention.
Figure 10B:
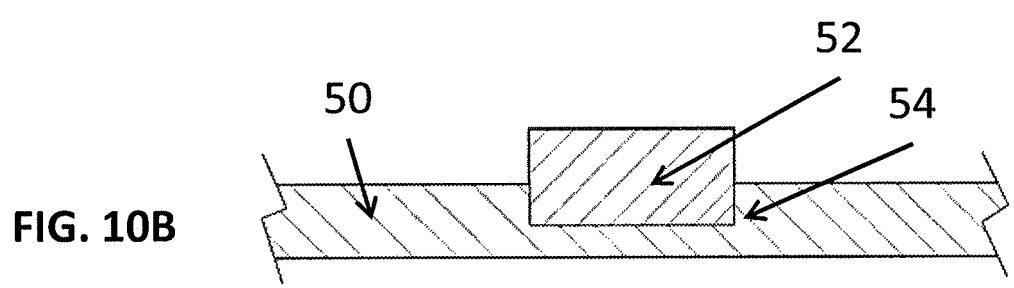
Figure 10C:
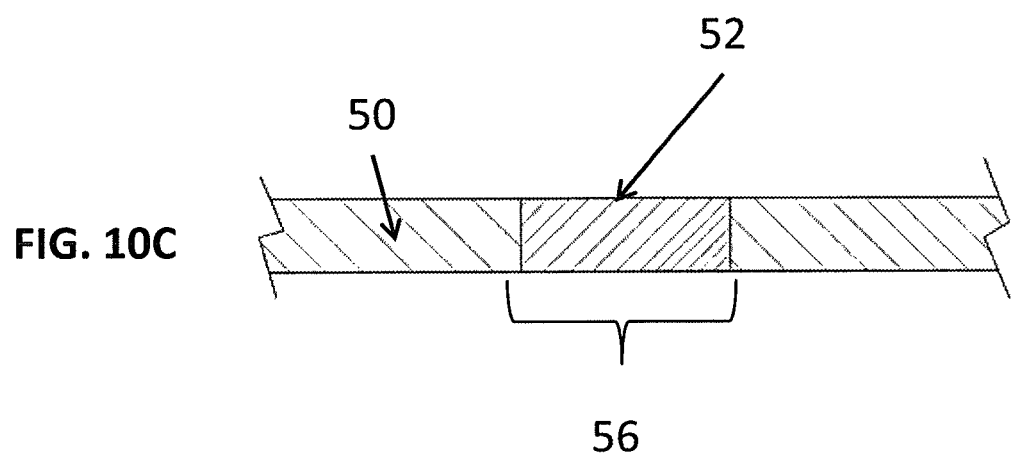

Referring to FIGS. 10A-10C, various arrangements of an indicator 52 being associated with a preform member 50 are shown. The preform member 50 and indicator 52 are substantially as described with respect to preform member 20 and indicator 26. FIG. 10A depicts the indicator 52 associated with, but not directly or indirectly coupled to, the preform member 50. In one embodiment, the indicator 52 of FIG. 10A is positioned in or near an apparatus for heating the preform member 50 and is physically separate from the preform member 50 (e.g., installed in a bath tank).

FIG. 10B depicts the indicator 52 positioned on a surface portion 54 on the preform member 50. As depicted, the surface portion 54 of the preform member 50 optionally partially defines a recess formed in the preform member 50, such that the indicator 52 extends partially through the thickness of the preform member 50. In FIG. 10C, the preform member 50 has an aperture 56 and the indicator 52 is positioned to traverse the aperture. Other suitable arrangements will be understood by one of skill in the art from the description herein.

Figure 11A:
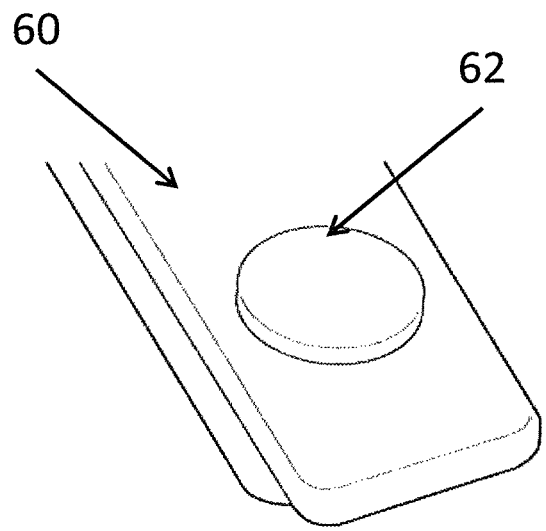
FIGS. 11A and 11B are isometric views of portions of an embodiment of a preform with an indicator and indicium according to aspects of the invention.
Figure 11B:
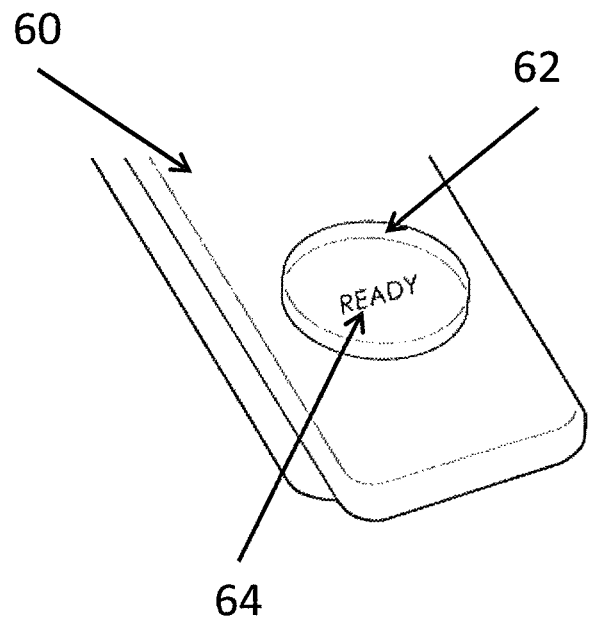

FIGS. 11A and 11B depict an indicator 62 positioned on a frame member 60 according to aspects of the invention. Alternatively, the indicator 62 may be positioned on the surface of a preform member or other components of a preform. The indicator 62 functions substantially as described with respect to indicator 26. At FIG. 11A, the indicator 62 has not been heated to the second temperature and is thus opaque with respect to the frame member 60. At FIG. 11B, however, the indicator 62 has been heated to the second temperature and is translucent with respect to the frame member 60.

According to embodiments of the invention, an indicium 64 may be positioned such that the indicium 64 is not visible when the indicator 62 is at the first temperature and is visible through the indicator 62 when the indicator 62 is at the second temperature. The indicium 64 may include, for example, text (such as "READY" shown in FIG. 11B), marks, symbols, a color(s), or any combination thereof. As depicted in FIG. 11B, the indicium 64 is positioned on a surface of the frame member 60. The indicium 64 may optionally be positioned on a surface of the indicator 62, disposed within the indicator 62, positioned on a surface of a preform member, etc.

Figures 12A, 12B, 12C:
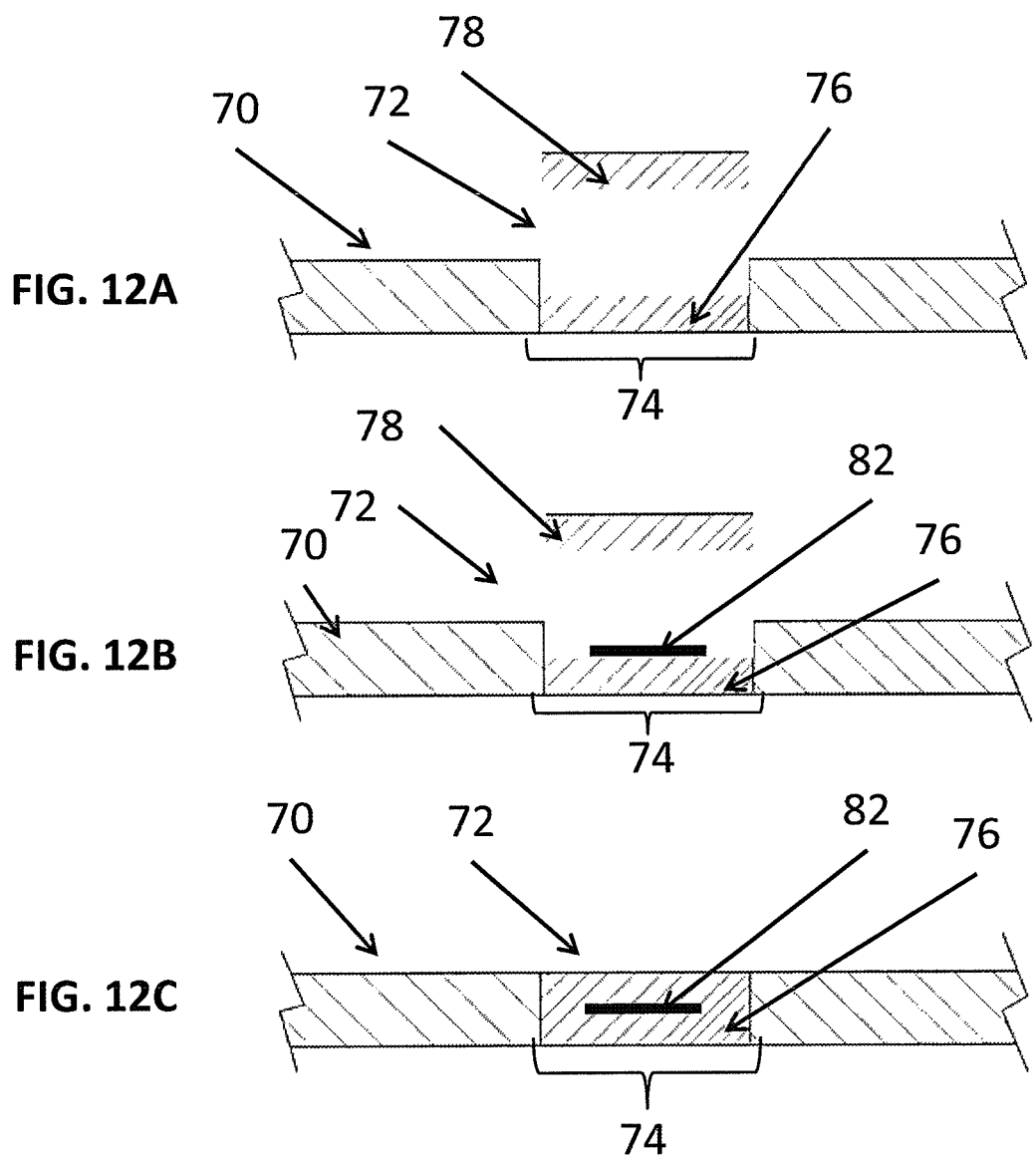
FIGS. 12A-12C are cross-sectional side views illustrating steps of an embodiment of a method for disposing an indicium within an indicator in accordance with aspects of the invention.

FIGS. 12A-12C depict various steps in a process for disposing an indicium 82 within an indicator 72 according to aspects of the invention. At FIG. 12A, a preform member 70 is shown. The preform member 70 may be of various thicknesses. In an embodiment, the preform member 70 is between about 1.6 mm thick to about 6.4 mm thick. Defined in the preform member 70 is an aperture 74. A bottom portion 76 of an indicator 72 at least partially traverses the aperture 74 and extends at least partially across the thickness of the preform member 70. In one embodiment, the bottom portion 76 is about one-half of the thickness of the preform member 70.

At FIG. 12B, an indicium 82 is disposed on a top surface of the bottom portion 76 of the indicator 72. The indicium 82 is substantially as described with respect to indicium 64. The indicium 82 may be disposed by printing, placing, etching, laminating, etc., and may be so positioned before or after the indicator is associated with the preform. Other suitable methods to dispose the indicium 82 will be understood by one of skill in the art from the description herein.

At FIG. 12C, a top portion 78 of the indicator 72 is disposed over the indicium 82. In one embodiment, the top portion 78 is of a thickness about one-half the thickness of the preform member 70. The indicium 82 may be laminated or otherwise applied to the top portion 78 as opposed to or in addition to the bottom portion 76. The top portion 78 is disposed within the aperture 72 of the preform member 70, thereby substantially traversing the aperture 72.

Methods for forming a preform described above into an immobilizer for use with a patient are now described in accordance with embodiments of the invention. A preform at a first temperature is used. The preform includes a preform member that is formed from thermoplastic materials and filler materials. The preform member is substantially or completely opaque at the first temperature and a second elevated temperature. The preform member is relatively rigid at the first temperature and can be formed at the second temperature. The preform also includes an indicator. The indicator has an appearance at the first temperature and a different appearance at the second temperature, wherein the indicator provides a visual indication of readiness to form the preform into the immobilizer upon heating the preform member to the second temperature at which the indicator has the different appearance. For example, the indicator is optionally substantially or completely opaque at the first temperature and substantially or completely translucent as compared to the preform member at the second temperature. At the second temperature, the indicator provides visual indication of the readiness to form the preform into the immobilizer by virtue of a contrast in the appearance of the indicator as compared to its appearance before reaching the second temperature and/or as compared to the appearance of the preform member.

First, the preform with the preform member and indicator is heated to the second temperature. The second temperature is preferably a temperature at which the preform member can be molded and the indicator is partially or completely translucent. The preform may be heated in a bath, oven, etc., by exposure to heat from a heat source such as heated liquid or gaseous fluid or other means for heating. Other suitable methods and apparatus for heating the preform will be understood by one of skill in the art from the description herein.

The indicator is then monitored while the preform is being heated from the first temperature to the second temperature. Once the indicator becomes translucent or otherwise adopts a different appearance such as by thermochromic dye or other color indicators, the preform member has reached the second temperature and as such can be molded. The indicator thus indicates readiness for further processing without requiring further delay.

The heating of the preform is then terminated after the indicator becomes translucent. Once the heating is terminated, the preform/preform member is removed from the heating apparatus and formed over a portion of a patient's anatomy. Because the indicator indicates readiness without requiring further processing delay, beneficial time savings can be achieved. For example, the preform can be removed from the heat source as soon as it is ready and without further delay, thus reducing the time for preparing the preform for forming, accelerating the availability of the heating apparatus (such as a water bath) to process more preforms, reducing the time a patient may need to wait before the preform is ready for forming, and shortening the time that equipment (such as medical imaging equipment) is used for a particular patient.

Once the preform is formed over a portion of a patient's anatomy, the indicator may be monitored again. In one embodiment, the indicator becomes substantially or completely opaque again when the preform cools from the second temperature. In such embodiments, when the indicator is opaque, the indicator provides visual indication that the preform member has transitioned back to being relatively rigid and can no longer be molded.

The forming of the preform into the immobilizer may then be terminated when, or soon after, the indicator becomes opaque. In some embodiments, the indicator becoming opaque does not necessarily mean that the mask can be removed. It is, however, an optional feature that turning opaque is one indicator that the preform is nearing the point when it can be removed.

Because the indicator indicates completion of forming without requiring further processing delay, beneficial time savings can also be achieved. For example, the preform can be removed from the patient as soon as it is ready and without further delay, thus reducing the time for preparing the immobilizer, accelerating the availability of the facilities in which the immobilizer is formed, reducing the time a patient may need to wait before the immobilizer is completed, and shortening the time that equipment (such as medical imaging equipment) is used for a particular patient.

The aforementioned steps for forming a preform into an immobilizer for use with a patient are exemplary and not exclusive. One of skill in the art will understand other suitable forming methods according to aspects of the invention from the description herein. Also, subsets of the steps may be performed, and the steps may be completed in various orders.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. An immobilization device having multiple sections formed from a low temperature thermoplastic, the immobilization device comprising:
    at least one preform section that does not become translucent when heated to an elevated temperature, the section being formed from a low temperature thermoplastic, the at least one preform section being more rigid at a non-elevated temperature and being moldable at the elevated temperature; and
    at least one indicator section that becomes translucent when heated to the elevated temperature at which the at least one preform section is moldable, thereby providing a visual indication of readiness for forming the at least one preform section and a visual indication for terminating the forming of the at least one preform section.

2. The immobilization device of claim 1 in which the at least one indicator section has a size greater than 1 mm^2.

3. The immobilization device of claim 1 in which an edge of the at least preform section is attached to an edge of the at least one indicator section.

4. The immobilization device of claim 1 wherein at least one preform section is perforated.

5. The immobilization device of claim 1 wherein at least one indicator section is perforated.

6. The immobilization device of claim 1, further comprising a frame, said frame having at least one indicator section embedded within it.

7. The immobilization device of claim 1, wherein the low temperature thermoplastic is a polycaprolactone based low temperature thermoplastic.

8. The immobilization device of claim 1, wherein the at least one preform section that does not become translucent further comprises at least one filler material.

9. The immobilization device of claim 1, wherein the low-temperature thermoplastic material does not contain a filler.

10. A method of preparing a preform to be formed into an immobilizer for a patient, the method comprising:
    heating a preform member of the preform from a first temperature at which the preform member is relatively rigid to a second temperature at which the preform member can be molded;
    monitoring an indicator associated with the preform member while heating the preform member, the indicator being formed from a thermoplastic material, the indicator being opaque at the first temperature and translucent at the second temperature, the method further comprising terminating the heating of the preform member after the indicator becomes translucent, thereby providing a visual indication of readiness to form the preform into the immobilizer.

11. The method of claim 10, wherein the low temperature thermoplastic of the preform member is a polycaprolactone based low temperature thermoplastic.

12. The method of claim 10, wherein the thermoplastic material that is opaque or substantially opaque at the first and second temperatures further comprises a filler material.

13. The method of claim 10, wherein the thermoplastic material of the preform member includes polycaprolactone.

14. An immobilization device comprising:
    a preform formed from a low temperature thermoplastic, the preform being moldable at an elevated temperature, the preform having multiple sections, the preform comprising:
        at least a first section of the preform that becomes translucent when heated to the elevated temperature, such that the first section provides a visual indication of the preform being moldable
    a frame, the frame being rigid at a non-elevated temperature and at the elevated temperature.

15. The immobilization device of claim 14, further comprising a second section of the preform, the second section of the preform having a filler material.

16. The immobilization device of claim 15, wherein the first section of the preform has less of the filler material than the second section of the preform.

17. A preform configured to be formed into an immobilizer for a patient, the preform comprising:
    a preform member that is relatively rigid at a first temperature and that is moldable at a second temperature that is elevated relative to the first temperature, the preform member being formed from a thermoplastic material and being opaque or substantially opaque at the first temperature and the second temperature;
    an indicator associated with the preform member and positioned to be monitored while heating the preform member, the indicator being formed from a thermoplastic material, the indicator being opaque at the first temperature and translucent at the second temperature;
    wherein the indicator is configured to provide a visual indication of readiness to form the preform into the immobilizer when the indicator becomes translucent.

18. The preform of claim 17, wherein the low temperature thermoplastic of the preform member is a polycaprolactone based low temperature thermoplastic.

19. The preform of claim 17, wherein the thermoplastic material that is opaque or substantially opaque at the first and second temperatures further comprises a filler material.

* * * * *